(12) United States Patent
Ishikawa

(10) Patent No.: US 11,515,017 B2
(45) Date of Patent: Nov. 29, 2022

(54) DELETION OF MEDICAL INFORMATION SHARED BETWEEN MANAGEMENT SERVER AND HEALTHCARE FACILITIES

(71) Applicant: Konica Minolta Healthcare Americas, Inc., Wayne, NJ (US)

(72) Inventor: Takayuki Ishikawa, Wayne, NJ (US)

(73) Assignee: Konica Minolta Healthcare Americas, Inc., Wayne, NJ (US)

( * ) Notice: Subject to any disclaimer, the term of this patent is extended or adjusted under 35 U.S.C. 154(b) by 119 days.

(21) Appl. No.: 17/163,933

(22) Filed: Feb. 1, 2021

(65) Prior Publication Data
US 2022/0246255 A1 Aug. 4, 2022

(51) Int. Cl.
*G16H 10/60* (2018.01)

(52) U.S. Cl.
CPC .................. *G16H 10/60* (2018.01)

(58) Field of Classification Search
CPC ........................................ G16H 10/60
See application file for complete search history.

(56) References Cited

U.S. PATENT DOCUMENTS

| 11,341,267 | B1 * | 5/2022 | Haverlah | G16H 40/67 |
| 2016/0098530 | A1 * | 4/2016 | Dill | G16H 10/60 705/3 |
| 2022/0013203 | A1 * | 1/2022 | Balignasay | G16H 30/20 |

FOREIGN PATENT DOCUMENTS

| CN | 112530582 A | * | 3/2021 | |
| EP | 3817002 A1 | * | 5/2021 | ......... G06F 21/6254 |

(Continued)

OTHER PUBLICATIONS

Article entitled "The freetext matching algorithm: a computer program to extract diagnoses and causes of death from unstructured text in electronic health records", by Shah et al., dated 2012 (Year: 2012).*

(Continued)

*Primary Examiner* — Mahesh H Dwivedi
(74) *Attorney, Agent, or Firm* — Osha Bergman Watanabe & Burton LLP

(57) ABSTRACT

The management server includes: a storage that stores medical information including patient-identity-specific information; and a processor coupled to the storage. The processor: receives patient-identity-specific information of a deceased patient; retrieves a deceased patient medical information; determines whether the deceased patient medical information includes a predetermined information that specifies a medical condition of the deceased patient; upon determining that the deceased patient medical information does not include the predetermined information, deletes the deceased patient medical information from the storage; upon determining that the deceased patient medical information includes the predetermined information: extracts the predetermined information along with the patient-identity-specific information of the deceased patient from the deceased patient medical information; separately stores the extracted predetermined information and the patient-identity-specific information of the deceased patient in the storage as a medical condition information; and deletes the deceased patient medical information after the extraction and storage of the medical condition information.

15 Claims, 12 Drawing Sheets

(56) References Cited

FOREIGN PATENT DOCUMENTS

JP          2004-021699 A       1/2004
JP             6692855 B2  *    5/2020    ............. G16H 10/60
WO     WO-2014061650 A1  *    4/2014    ........... G06F 19/321

OTHER PUBLICATIONS

Article entitled "Automatic ICD-10 Classification of Cancers from Free-Text Death Certificates", by Koopman et al., dated Aug. 10, 2015 (Year: 2015).*
Article entitled "Automatic Classification of Free-Text Medical Causes from Death Certificates for Reactive Mortality Surveillance in France", by Baghdadi et al., dated Jun. 24, 2019. (Year: 2019).*

* cited by examiner

FIG. 2

| PATIENT ID | LIFE FLAG | HISTORY FLAG | PATIENT NAME | GENDER | DOB |
|---|---|---|---|---|---|
| Patient1 | 1 | 1 | Bob | M | 10/10/1980 |
| Patient2 | 2 | 1 | Tim | M | 12/13/1940 |
| Patient3 | 2 | 2 | Jenny | F | 3/18/1950 |
| ... | ... | ... | ... | ... | ... |

FIG. 3

| EXAM ID | PATIENT ID | MEDICAL IMAGE | REPORT DATA |
|---|---|---|---|
| 111 | Patient1 | DICOM1 | Report1 |
| 222 | Patient2 | DICOM2 | Report2 |
| 333 | Patient3 | DICOM3 | Report3 |
| ... | ... | ... | ... |

FIG. 4

| EXAM ID | ORDER ID | EXAMINATION DATE | EXAMINATION SITE | DOCTOR |
|---|---|---|---|---|
| 111 | Order1 | 04/16/2015 | Brain | M. Smith |
| 222 | Order2 | 07/06/2016 | Lung | M. Smith |
| 333 | Order3 | 09/26/2017 | Heart | K. Michael |
| ... | ... | ... | ... | ... |

FIG. 5

| PATIENT ID | LIFE FLAG |
|---|---|
| Patient1 | 1: Alive |
| Patient2 | 2: Dead |
| Patient3 | 2: Dead |

FIG. 6

| PATIENT ID | HISTORY FLAG |
|---|---|
| Patient1 | 1: Yes |
| Patient2 | 1: Yes |
| Patient3 | 2: No |

FIG. 7E

Smith, Todd  DOB: 1985/12/31  MRN: SA33-3333

Facilities

Account No.

*Name  Smith  Todd

*DOB  19851231

Smoking Status

Racial/Ethnic

Physician

Home Address

STATUS  Dead ▼
Alive

Sex  M ▼
Height (ft/in)  5.5
Weight (lbs.)  140
Language  Eng. ▼

FIG. 7F

Smith, Todd  DOB: 1985/12/31  MRN: SA33-3333

Facilities

Account N

Name

DOB

Smoking S

Racial/Eth

Physician

Home Address

STATUS  Dead ▼
Alive

REGISTER DECEASE INFORMATION?

YES   NO   CANCEL

Language

| PATIENT ID | PATIENT NAME | GENDER | DOB | MEDICAL IMAGE |
|---|---|---|---|---|
| Patient1 | Bob | M | 10/10/1980 | DICOM1 |
| Patient2 | 09102020 | M | 1/1/1940 | DICOM2 |
| ~~Patient3~~ | ~~Jenny~~ | ~~F~~ | ~~3/18/1950~~ | ~~DICOM3~~ |
| ... | ... | ... | ... | ... |

DELETION OF MEDICAL INFORMATION SHARED BETWEEN MANAGEMENT SERVER AND HEALTHCARE FACILITIES

BACKGROUND

Medical images and medical data (herein collectively referred to as "medical information") play a crucial role in a healthcare professional's diagnosis of a patient. Healthcare facilities (e.g., hospitals) have realized the benefits of electronically storing these medical information. This digitalization of medical information not only enables healthcare professionals to easily access the medical information, but also enables the medical information to be easily shared between multiple healthcare facilities through use of physical mediums such as compact discs (CDs), digital video discs (DVDs), and Universal Serial Bus (USB) flash drives.

More recently, cloud-based storage systems have emerged as a way to improve efficiency and accessibility to information. In general, a "cloud" can be understood as an online storage system that provides remote, on-demand access of computing resources and data over the Internet to multiple computers and devices in various locations. Cloud-based storage may be provided by vendors who use remote or off-site data centers in various locations for storage of data such as medical images. The vendors of the cloud-based storage may also provide a common viewing system ("a universal viewer") that allows healthcare facilities within the cloud network to retrieve a complete set of any patient's medical information from any other healthcare facility within the cloud network through a single request.

However, these digitalized medical information are usually set to be automatically deleted after a certain time has elapsed once a patient dies. For example, a deceased patient's medical information would be deleted after a certain time has passed since the patient's passing and would no longer be able to be utilized.

SUMMARY

One or more embodiments of the invention provide a management server, a method, and a non-transitory computer-readable medium (CRM) for controlling deletion of medical information shared between the management server and healthcare facilities connected to the management server.

One or more embodiments provide a management server that communicates with a healthcare facility, the management server comprising: a storage that stores medical information including patient-identity-specific information; and a processor coupled to the storage, wherein the processor: receives patient-identity-specific information of a deceased patient; retrieves, from among the medical information in the storage, a deceased patient medical information using the patient-identity-specific information of the deceased patient; determines whether the deceased patient medical information includes a predetermined information that specifies a medical condition of the deceased patient; upon determining that the deceased patient medical information does not include the predetermined information, deletes the deceased patient medical information from the storage; upon determining that the deceased patient medical information includes the predetermined information: extracts the predetermined information along with the patient-identity-specific information of the deceased patient from the deceased patient medical information; separately stores the extracted predetermined information and the patient-identity-specific information of the deceased patient in the storage as a medical condition information; and deletes the deceased patient medical information after the extraction and storage of the medical condition information; and transmits, upon receiving a medical condition information retrieval request from the healthcare facility, the medical condition information to the healthcare facility to be displayed on a display of the healthcare facility.

One or more embodiments provide a method for controlling deletion of medical information from a storage of a management server that communicates with a healthcare facility, the storage storing medical information including patient-identity-specific information, the method comprising: receives a patient-identity-specific information of a deceased patient; retrieves, from among the medical information in the storage, a deceased patient medical information using the patient-identity-specific information of the deceased patient; determining whether the deceased patient medical information includes a predetermined information that specifies a medical condition of the deceased patient; upon determining that the deceased patient medical information does not include the predetermined information, deleting the deceased patient medical information from the storage; upon determining that the deceased patient medical information includes the predetermined information: extracting the predetermined information along with the patient-identity-specific information of the deceased patient from the deceased patient medical information, separately storing the extracted predetermined information and the patient-identity-specific information of the deceased patient in the storage as a medical condition information, and deleting the deceased patient medical information after the extraction and storage of the medical condition information; and transmitting, upon receiving a medical condition information retrieval request from the healthcare facility, the medical condition information to the healthcare facility to be displayed on a display of the healthcare facility.

One or more embodiments provide a non-transitory computer-readable medium (CRM) storing an instruction to control deletion of medical information from a storage of a management server that communicates with a healthcare facility, the storage storing medical information including patient-identity-specific information, the instruction causing a management server to: receive a patient-identity-specific information of a deceased patient; retrieve, from among the medical information in the storage, a deceased patient medical information using the patient-identity-specific information of the deceased patient; determine whether the deceased patient medical information includes a predetermined information that specifies a medical condition of the deceased patient; upon determining that the deceased patient medical information does not include the predetermined information, delete the deceased patient medical information from the storage; upon determining that the deceased patient medical information includes the predetermined information: extract the predetermined information along with the patient-identity-specific information of the deceased patient from the deceased patient medical information, separately store the extracted predetermined information and the patient-identity-specific information of the deceased patient in the storage as a medical condition information, and delete the deceased patient medical information after the extraction and storage of the medical condition information; and transmit, upon receiving a medical condition information retrieval request from the healthcare facility, the medical condition information to the healthcare facility to be displayed on a display of the healthcare facility.

Other aspects and advantages of the invention will be apparent from the following description and the appended claims.

BRIEF DESCRIPTION OF DRAWINGS

FIG. 2 shows a table of a database stored in a management server according to one or more embodiments.

FIG. 3 shows another table of the database stored in the management server according to one or more embodiments.

FIG. 4 shows another table of the database stored in the management server according to one or more embodiments.

FIG. 5 shows another table of the database stored in the management server according to one or more embodiments.

FIG. 6 shows another table of the database stored in the management server according to one or more embodiments.

FIGS. 7A-7F show example screens of a system according to one or more embodiments.

FIGS. 8A-8E show other example screens of the system according to one or more embodiments.

FIG. 9 shows another table of the database stored in the management server according to one or more embodiments.

DETAILED DESCRIPTION

Figure 1:
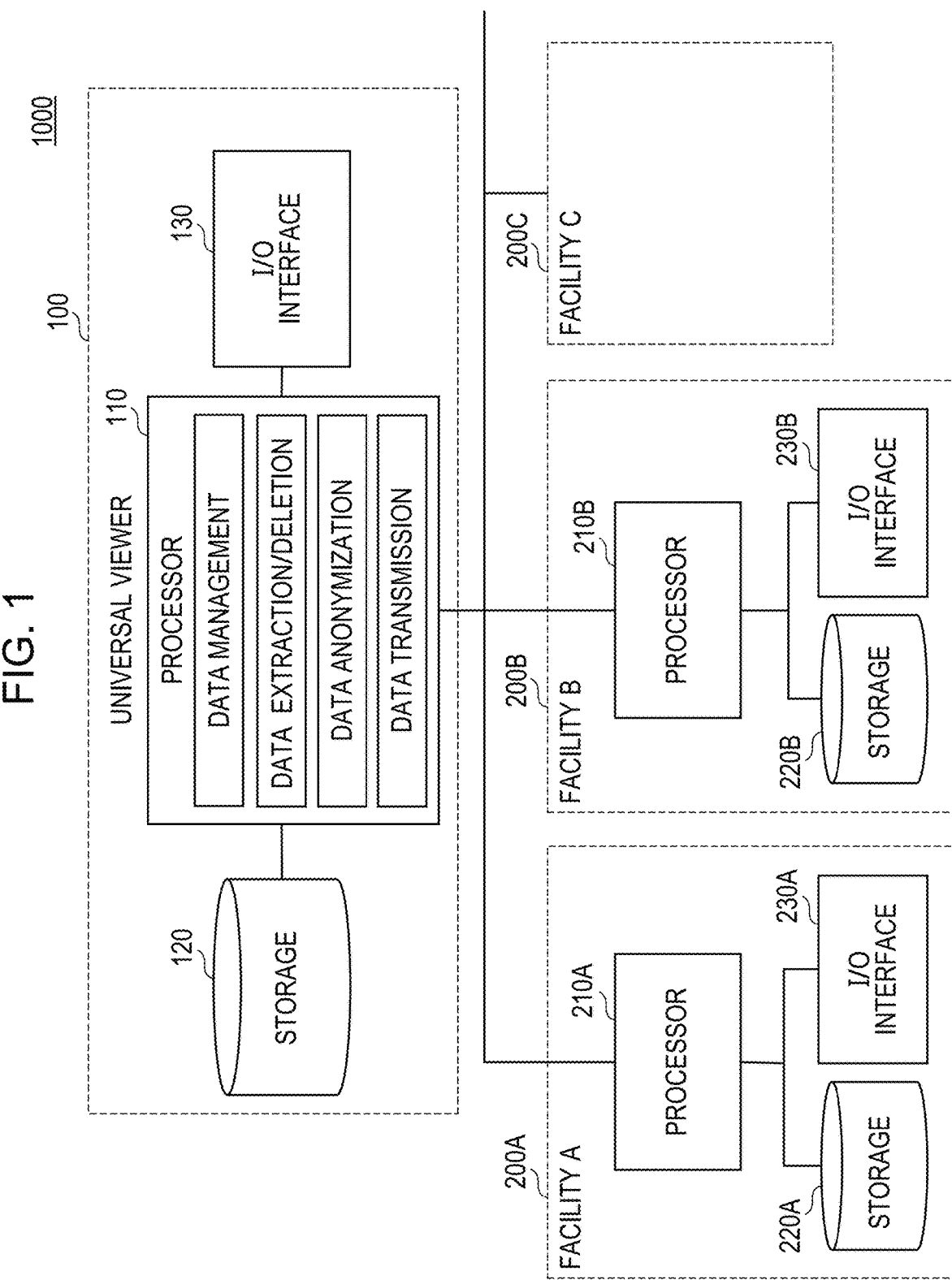
FIG. 1 shows a system according to one or more embodiments.

Specific embodiments will now be described in detail with reference to the accompanying figures. Like elements in the various figures are denoted by like reference numerals for consistency. Like elements may not be labeled in all figures for the sake of simplicity.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers does not imply or create a particular ordering of the elements or limit any element to being only a single element unless expressly disclosed, such as by the use of the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "a horizontal beam" includes reference to one or more of such beams.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Although multiple dependent claims are not introduced, it would be apparent to one of ordinary skill that the subject matter of the dependent claims of one or more embodiments may be combined with other dependent claims.

[System Overview]

In general, one or more embodiments of the invention provide a management server, a method, and non-transitory computer-readable medium (CRM) for controlling deletion of medical information shared between the management server (e.g., a cloud server) and healthcare facilities connected to the management server through a medical information sharing system (e.g., a universal viewer system).

The management server includes a universal viewer computing device installed with a universal viewer application. The universal viewer computing device may be an industrial-use computer that includes one or more computer processors, associated memory (e.g., random access memory (RAM), cache memory, flash memory, etc.), one or more storage devices (e.g., a hard disk, an optical drive such as a compact disk (CD) drive or digital versatile disk (DVD) drive, a flash memory stick, etc.), and numerous other elements and functionalities. The universal viewer computing device may be managed by the vendor(s) that provide the services of the cloud-based PACS.

The management server centrally manages medical information of patients obtained from examinations (e.g., computerized tomography (CT), magnetic resonance imaging (MRI), etc.) and diagnoses conducted at the healthcare facilities. Upon receiving a retrieval request from any one of the healthcare facilities, the management server transmits the medical information to the requesting healthcare facility (or facilities) so that the medical information can be displayed to a user at the requesting healthcare facility. The user can in turn view the medical information and use the medical information during a patient's medical examination/treatment. A "user" may be any healthcare professional such as a doctor, nurse, medical staff, medical technician, etc.

In one or more embodiments, the management server and the healthcare facilities may be associated with one of a cloud-based storage system, a Picture Archiving and Communication System (PACS), and a cloud-based PACS provided by a same or a different vendor.

In one or more embodiments, a patient's medical images may be stored in a Digital Imaging and Communications in Medicine (DICOM) format image. The DICOM format image may include a patient's medical data in the form of metadata. A patient's medical data may include patient-identity-specific information (e.g., patient ID, patient name, patient date of birth (DOB), patient gender, etc.) and examination-specific information (e.g., a date of an examination, accession number of each medical image, types of modalities used to perform the examination, etc.). The patient's medical data may also be separately stored in the form of an electronic document (e.g., OOXML document, PDF document, etc.).

[System Structure]

FIG. 1 shows a system (1000) in accordance with one or more embodiments. As shown, the system (1000) includes a management server (100) and Facilities A-C (i.e., healthcare facilities). Facilities A-C are connected to one another via a network such as the Internet, and may be any type of facility that provides medical care (e.g., a public hospital, a private hospital, a medical clinic, a dental clinic, an emergency vehicle (e.g., ambulance), a mobile clinic vehicle, etc.). In one or more embodiments, the number of the healthcare facilities is not limited to three as shown in FIG. 1 and any number of healthcare facilities may be interconnected through the management server (100).

[Management Server]

The management server (100) may be a cloud server or may be a local server installed at any one of Facilities A-C. The management server (100) centrally manages medical information transmitted from Facilities A-C. In the disclosure, medical information of a deceased patient will be separately referred to as a deceased patient medical information. The management server (100) extracts a predetermined information that specifies a medical condition of the deceased patient along with a patient-identity-specific information that identifies the deceased patient from among the deceased patient medical information. The management server (100) then separately stores the extracted predetermined information and patient-identity-specific information as a medical condition information of the deceased patient. Upon receiving a medical condition information retrieval request from any one of Facilities A-C, the management server (100) transmits the requested medical condition information to the requesting ones among Facilities A-C so that the medical condition information can be available for use and display at these facilities.

The predetermined information may be information about a specific cause of death and/or medical history information of the deceased patient, which will be described in more detail below with reference to FIGS. 8A-8B. Further, the predetermined information may include one or more specified items such as a diagnosis report, a disease-related medical image, and/or a medication history of the deceased patients. These will also be described in more detail below with reference to FIGS. 8A-8B.

As shown in FIG. 1, the management server (100) includes a processor (110), a storage (120), and an I/O interface (130). The management server (100) may also include a cloud gateway (GW) device. The cloud GW device may be a hub or a local area network (LAN) at the facility where the management server (100) is physically disposed. The cloud GW device may be configured as a relay point disposed between the management server (100) and Facilities A-C and enabling each of Facilities A-C to communicate and share the medical information with the management server (100).

The processor (110) may be configured with a Web-Client (web-CL) application for the universal viewer computing device. The web-CL client allows Facilities A-C to access the universal viewer application via a web-browser. For example, the universal viewer application may be accessed as a web page by inputting a uniform resource locator (URL) (e.g., a web address) associated with the web-CL into a search bar of a web-browser.

Furthermore, the processor (110) has: a data management function; data extraction/deletion function; data anonymization function; and data transmission function, which are described later. The web-CL and these functions may be applications and programs configured to be executed by the processor (110).

The storage (120) is configured as a remote medical repository that stores a database remotely on the management server (100). For example, the remote medical repository may be a virtual data room (VDR) or a database (or group of databases) accessed remotely via the Internet.

The database of the storage (120) stores the medical information, which may be inputted by the user via the I/O interface (130) and/or transmitted from Facilities A-C.

The database also stores a patient's status information (herein referred to as "status information") and a deceased patient's decease information (herein referred to as "decease information") as part of the medical information. The status and decease information may be inputted by the user via the I/O interface (130) and/or transmitted from Facilities A-C. The status information indicates whether a patient recorded in the management server (100) is dead (i.e., deceased) or alive. The decease information may be a death certificate or similar type of information that provides information on the death of the deceased patient (e.g., a date of death; a cause of death; the name of the deceased; a place of death, etc.).

In one or more embodiments, the I/O interface (130) may include an input device such as a touchscreen, keyboard, mouse, microphone, touchpad, electronic pen, or any other type of input device. The I/O interface (130) may also include an output device such as a screen (e.g., a liquid crystal display (LCD), a plasma display, touchscreen, cathode ray tube (CRT) monitor, projector, or any other display device), a printer, external storage, or any other output devices.

[Healthcare Facilities]

As shown in FIG. 1, the system (1000) further includes local computing devices (200A-200C) (i.e., local computers) in Facilities A-C. Each of the local computing devices (200A-200C) may correspond to a personal computer (PC), a laptop, a mobile computing device (e.g., tablet PC, smartphone, etc.), a server, a mainframe, a kiosk, etc. Because the local computing devices (200A-200C) in Facilities A-C have similar structures, for brevity, only the local computing device (200A) in Facility A will be explained.

The local computing device (200A) includes a processor (210A), storage (220A), and I/O interface (230A). The local computing device (200A) may further include a local GW device (not-illustrated) that synchronizes the locally-managed and stored data to the management server (100). The local computing device (200A) may also include a universal viewer client application (not-illustrated) that causes the I/O interface (230A) to display contents associated with the universal viewer client application and receives input commands from the I/O interface (230A).

The processor (210A) manages the medical information in the storage (220A). Further, the processor (210A) transmits the medical condition information retrieval request to the management server (100) based on inputs by the user via the I/O interface (230A). The medical condition information retrieval request may include a search request key including a patient-identity-specific information that identifies the specific patient whose medical information is being requested.

Upon receiving the requested medical condition information from the management server (100), the processor (210A) may store the medical condition information in the storage (220A) and/or display the medical condition information on the I/O interface (230A).

In one or more embodiments, the storage (220A) may store the medical information obtained from examinations and/or diagnoses performed at Facility A and the medical condition information received from the management server (100). Furthermore, the I/O interface (230A) may have similar functions and structures as that of the I/O interface (130).

FIGS. 2-6 show example tables of a medical information database stored in the storage (120) according to one or more embodiments.

FIG. 2 shows a table displaying the medical information in one format according to one or more embodiments. As shown, each medical information may include the patient-identity-specific information such as: PATIENT ID, PATIENT NAME, GENDER, and DOB.

The medical information may also include the status information (e.g., the LIFE FLAG) and the medical history information (e.g., the HISTORY FLAG) indicating whether a patient has previously had a serious illness in the patient's medical history. Alternatively, instead of the HISTORY FLAG, the medical information may include a column indicating whether information relating to a specific cause of death is available.

In the example shown in FIG. 2, a "1" under the LIFE FLAG column indicates that the patient is alive while a "2" indicates that a patient is deceased. Additionally, a "1" under the HISTORY FLAG column indicates that a patient previously had a serious illness while a "2" indicates that a patient did not previously have a serious illness. In one or more embodiments, a HISTORY FLAG of "1" indicates that the medical information includes the predetermined information.

FIG. 3 shows another table displaying the medical information in another format according to one or more embodiments. As shown, each medical information may include one or more medical images ("DICOM 1," "DICOM 2," "DICOM 3," etc.) and one or more report data ("Report 1," "Report 2," "Report 3," etc.). Each medical image and report data are correlated to an examination ID ("111," "222," "333," etc.) and patient ID ("Patient 1," "Patient 2," "Patient 3," etc.).

FIG. 4 shows another table displaying the medical information in yet another format according to one or more embodiments. As shown, each medical information may include examination-specific information such as: an examination ID ("111," "222," "333," etc.), an examination order ID ("Order 1," "Order 2," "Order 3," etc.), an examination date ("Apr. 15, 2016," "Jul. 6, 2016," "Sep. 26, 2017," etc.), an examination site ("Brain," "Lung," "Heart," etc.), and a doctor who performed the examination ("M. Smith," "M. Smith," "K. Michael," etc.).

FIG. 5 shows another table displaying the medical information in yet another format according to one or more embodiments. The format shown in FIG. 5 includes only the patient ID and the LIFE FLAG as discussed above in reference to FIG. 2.

FIG. 6 shows another table displaying the medical information in yet another format according to one or more embodiments. The format shown in FIG. 6 includes only the patient ID and the HISTORY FLAG as discussed above in reference to FIG. 2. In one or more embodiments, information about the serious illnesses may be previously set via the I/O interface (130) and stored in the storage (120).

In one or embodiments, the formats shown in FIGS. 2-6 may be combined and are not limited to only the information shown in each figure. For example, a table displaying the medical information may include any combination of the formats shown in FIGS. 2-6 with any one of (or more than one of) the columns removed.

[System Functions]

Next, the functions of the system (1000) will be described with reference to FIGS. 7A-7F and 8A-8E. Hereinafter an example of how the management server (100) extracts medical condition information from a deceased patient medical information and transmits the medical condition information in response to a medical condition information retrieval request from the local computing device (200A) at Facility A will be described. The example screens shown in FIGS. 7A-7F and 8A-8E are displayed on the I/O interface (130) of the management server (100). Similar operations can be also performed on screens displayed on the I/O interface (230A) of the local computing device (200A) via the network.

A user of Facility A may confirm that a patient is deceased by asking the patient's family, or through various other means. The user then logs into the management server (100) through the local computing device (200A) by inputting a user ID and password into the predetermined fields of a login screen shown in FIG. 7A. Once the user is logged in, the user is directed to a menu screen shown in FIG. 7B.

Figures 7A, 7B:
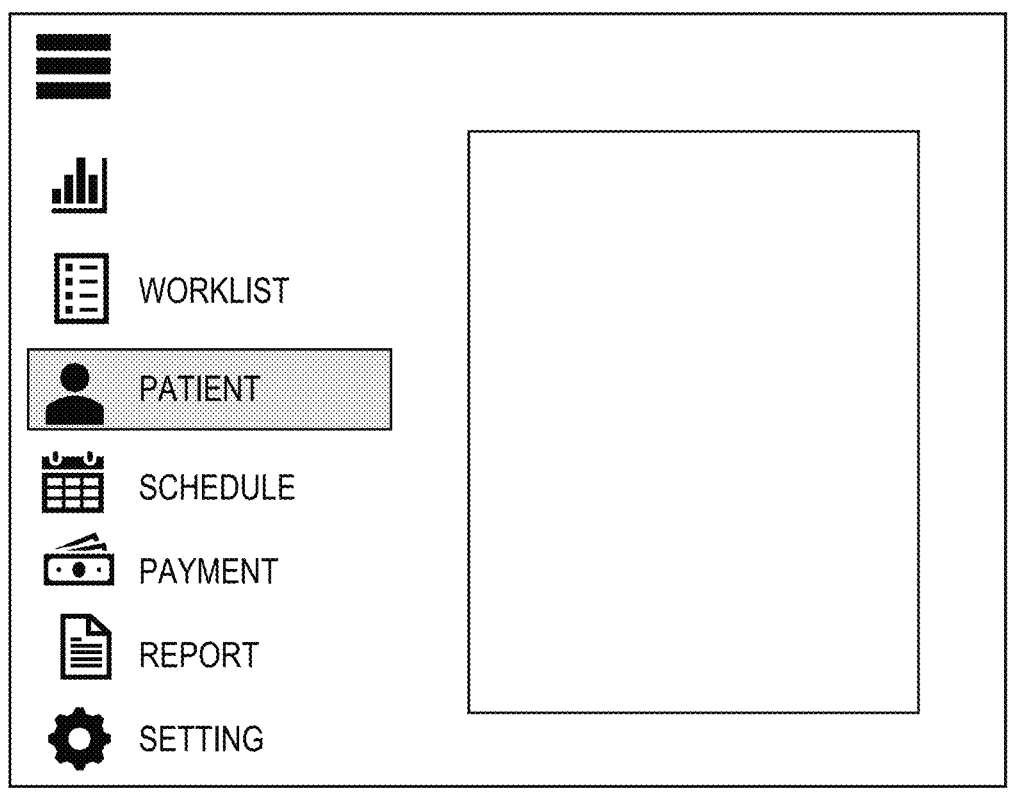
Figure 7C:
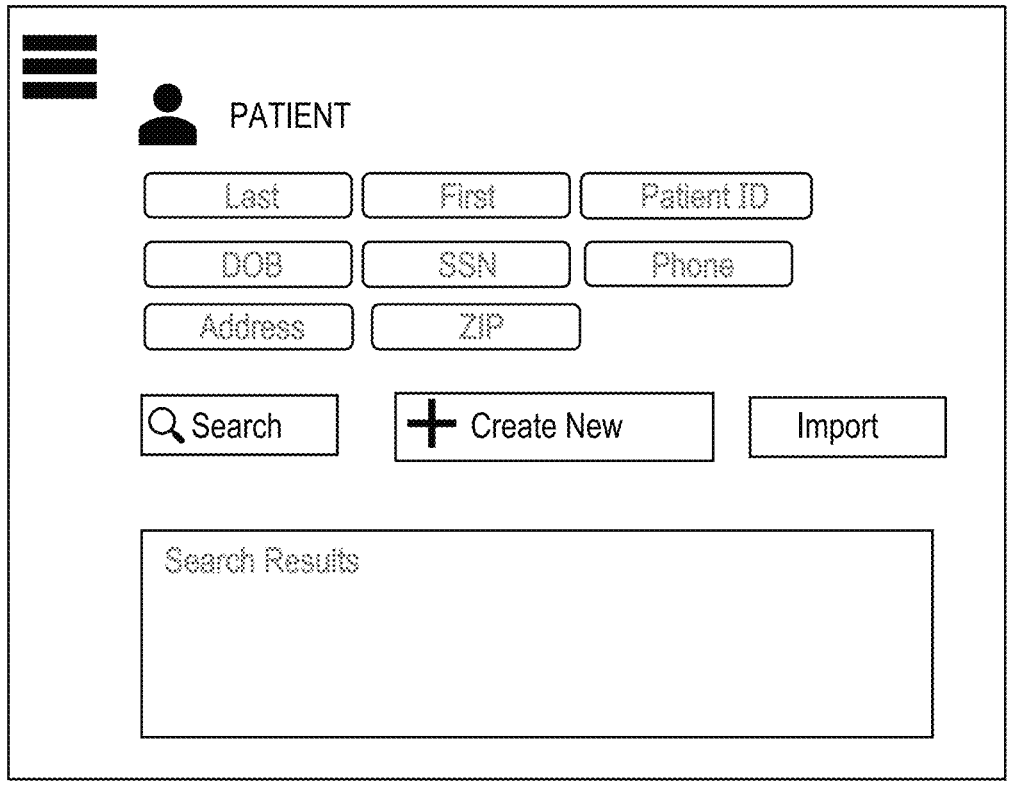

When the user clicks the PATIENT button on the menu screen of FIG. 7B, the user is transferred to a patient information screen shown in FIG. 7C. The patient information screen includes fields of the patient-identity-specific information including: a last name; first name; patient ID; DOB; Social Security Number (SSN); phone number; address; and zip code. Once the patient information screen of FIG. 7C is displayed, the user inputs the deceased patient's patient-identity-specific information.

Figure 7D:
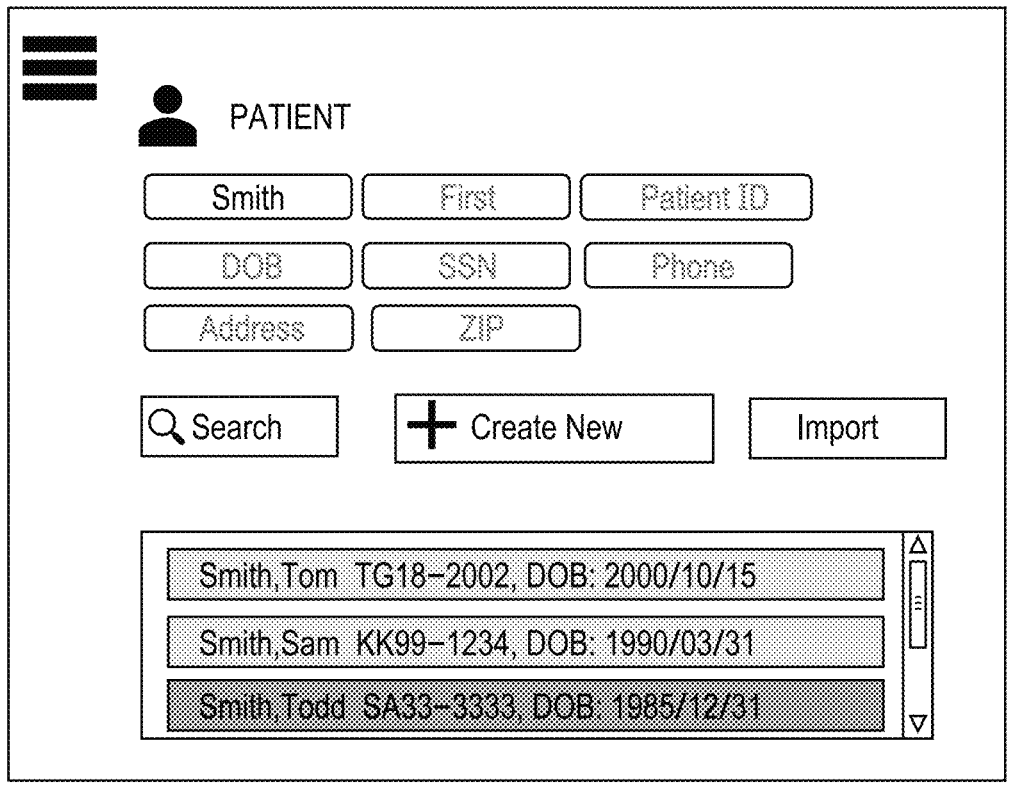

Upon receiving the patient-identity-specific information of the deceased patient from the local computing device (200A), the processor (110) of the management server (100) searches (using the patient-identity-specific information as a key) for the deceased patient medical information in the storage (120) and displays the deceased patient medical information to the user. For example, when the user inputs a patient-identity-specific information such as "Smith" in the last name field and clicks on the search button, a search request is transmitted from the local computing device (200A) to the server (100). In response, medical information for patients with the last name "Smith" are displayed in an itemized list as shown in FIG. 7D. When the user clicks on one of the files (e.g., file of "Smith, Todd"), the deceased patient medical information of "Smith, Todd" is displayed on an edit screen as shown in FIG. 7E.

As shown in FIG. 7E, the edit screen includes input fields such as: facilities; account number; name; DOB; smoking status; racial/ethnic; physician; home address; status (i.e., dead or alive); sex; height; weight; and language. Each of these input fields corresponds to a patient-identity-specific information of the deceased patient. Additionally, any of the input fields may be edited by the user.

As shown in FIG. 7F, when the user clicks a predetermined button (e.g., enter button or exit button) on the edit screen, the user is presented with a pop-up menu that asks whether to register the decease information. If the user clicks on the CANCEL button, the user is brought back to the edit screen. If the user clicks on the NO button, the processor (110) registers only the existing status information in the storage (120) and the user is taken to an extraction screen shown in FIG. 8A. If the user clicks on the YES button, a separate input screen (not shown) is displayed where the user can input the decease information. Upon receiving the inputted decease information, the processor (110) stores the decease information in the storage (120) and displays the decease information on the extraction screen. This enables the use of the decease information as the part of the deceased patient medical information. Even when the decease information is not input, at least the existing status information is registered. This enables searching the deceased patient medical information from among the medical information.

Figures 8A, 8B:
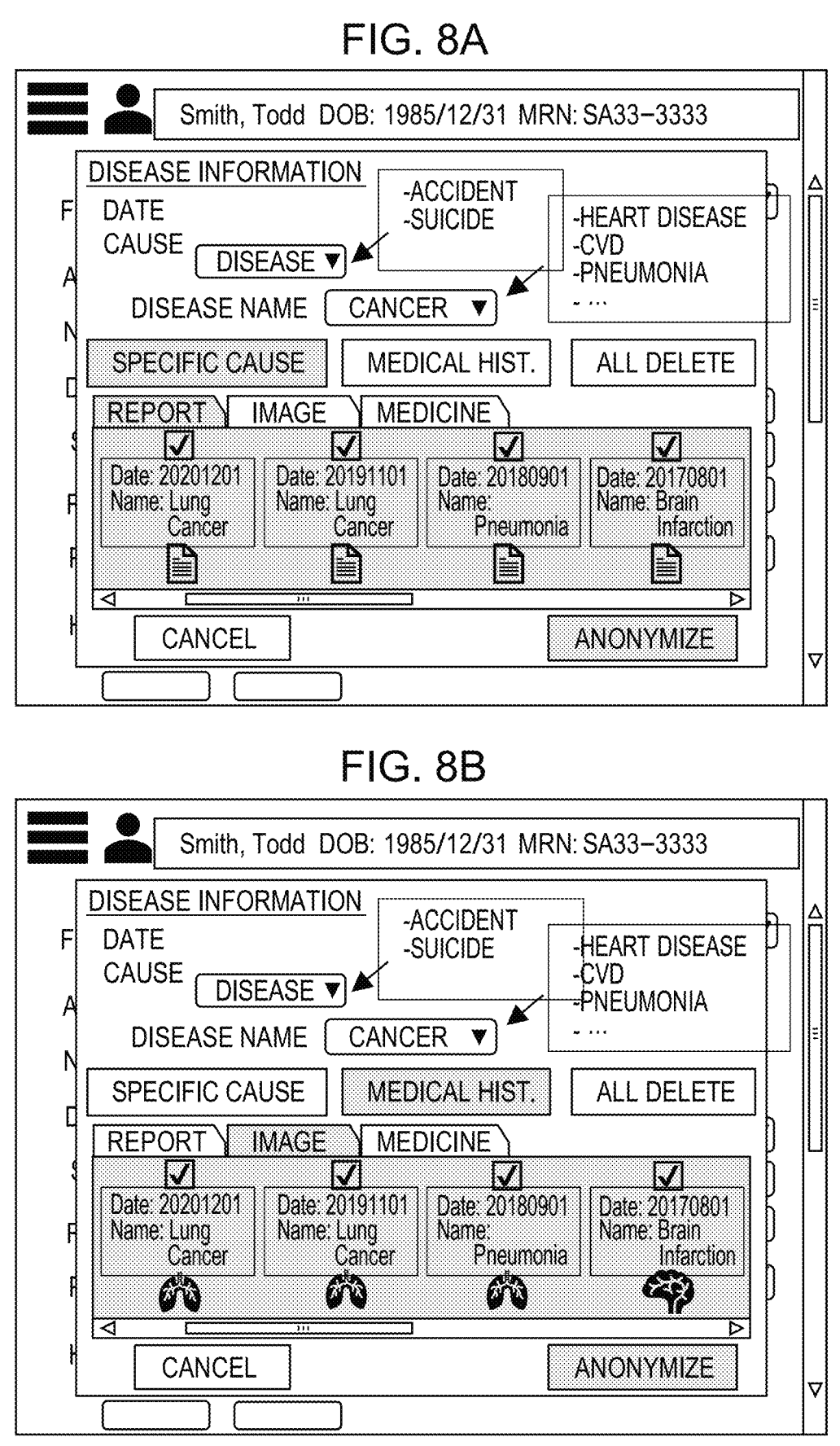

Once the extraction screen of FIG. 8A is displayed, the processor (110) starts a process that determines whether the deceased patient medical information includes the predetermined information that can be used to identify a medical condition of the deceased patient. The processor may start the determination process after receiving a start command from the user. For example, the processor (110) may start the determination process after the user clicks the SPECIFIC CAUSE button in FIG. 8A or the MEDICAL HIST. button in FIG. 8B. Alternatively, the processor may automatically start the determination process upon receiving information that the patient is deceased (e.g., upon receiving the decease information entered on the input screen of FIG. 7F).

In one or more embodiments, as discussed above in reference to FIG. 1, the predetermined information may include the information about the specific cause of death and/or the medical history information of the deceased patient. The specific cause of death may be information such as: a disease identified as resulting in the patient's death, a disease contracted by the patient right before a patient's death, diseased contracted by the patient during a predetermined period (e.g., 3 months) before the patient's death, an accident the patient was involved in, a suicide, etc. The medical history information may include information such as: a disease site; disease-related medical image; a diagnosis report; a patient's surgery history; a patient's treatment period and record; a patient's medication history; etc.

The processor (110) determines whether the deceased patient medical information includes the predetermined information by searching the deceased patient medical information for one or more specific disease names (e.g., "cerebral infarction due to embolism of precerebral arteries") and/or specific disease codes (e.g., a combination of specific character(s)/number(s)) each identifying a disease (e.g., cancer, heart disease, cerebrovascular disease (CVD), etc.) that could cause death. The specific disease name and specific disease code are stored in a specific field of the medical information.

If it is determined that the deceased patient medical information does not include the predetermined information, the processor (110) deletes the deceased patient medical information from the storage (120). This advantageously conserves memory space in the system (1000) because a user (e.g., a physician) would no longer have a need for such deceased patient medical information after the patient's death.

Conversely, if it is determined that the deceased patient medical information includes the predetermined information, the processor (110) extracts the predetermined information along with the patient-identity-specific information of the deceased patient from the deceased patient medical information. Once the extraction is complete, the processor (110), displays the extracted predetermined information and patient-identity-specific information on the extraction screen. The processor (110) then separately stores the extracted predetermined information and patient-identity-specific information in the storage (120) as the medical condition information of the deceased patient and deletes the remaining deceased patient medical information.

Moreover, after determining that the deceased patient medical information includes the predetermined information, the processor (110) initiates a timer and determines whether a predetermined time has elapsed since the start of the timer. The predetermined time may be set via the I/O interface (130) and stored in the storage (120). When the predetermined time elapses, the processor (110) categorizes the deceased patient medical information as less-useful information not necessary for medical examination/treatment and deletes the deceased patient medical information regardless of whether the predetermined information has been extracted. This advantageously conserves memory space in the system (1000) by retaining only information deemed useful by the user. In particular, the predetermined item specifies the medical condition of the deceased patient, which could be useful for treatments/diagnosis of family members of the deceased patient (e.g., determining the family member's condition if the medical condition of the deceased patient is hereditary, etc.).

In one or more embodiments, as discussed above in reference to FIG. 1, the predetermined information may include the specified item such as the diagnosis report, the disease-related medical image, and/or the medication history. The diagnosis report is an existing medical report created by a doctor that includes a condition of a disease contracted by the deceased patient. The disease may be one contracted throughout the deceased patient's lifetime and is not limited to the disease that caused the patient's death. The medical image may be a medical image, or a set of medical images, taken for each disease in the diagnosis report. The medication history may be a record (e.g., a medication reports) of medicine and medication guidance administered to the patient with respect to the disease documented in the diagnosis report.

In one or more embodiments, the processor (100) may receive an input from the user to search for the specified item. The extraction screen of FIG. 8A includes options (e.g., the SPECIFIC CAUSE and MEDICAL HIST. buttons) for the user to enable a search for the specified items during the extraction. The extraction screen further includes options for the user to select the type of specified item to be searched for in the predetermined information. For example, as shown in FIG. 8A, the extraction screen includes a REPORT tab showing a list of medical reports. The medical reports under the REPORT tab are examples of diagnosis reports that qualify as the specified item. As further shown in FIG. 8A, the user has selected all the medical reports under the REPORT tab. As a result, the processor (110) will search the predetermined item for these selected medical reports and extract these medical reports if they are found. As another example, the user may click on the IMAGE tab on the extraction screen of FIG. 8B and select specific medical images to be searched for within the predetermined information. As yet another example, the user may click on the MEDICINE tab shown in FIG. 8B to search the predetermined information for specific information (e.g., medication reports) related to the deceased patient's medication history. In one or more embodiments, only the selected medical reports, medical images, and medication history are searched for and extracted from the predetermined information. All unselected items will be deleted with the deceased patient medical information when the processor (100) completes the extraction. This advantageously conserves memory space in the system (1000) while retaining only specific information (e.g., the specified item that the user selected) the user deems necessary for future treatments/diagnoses. In particular, the specified item specifies the medical condition of the deceased patient, which could be useful for treatments/diagnosis of family members of the deceased patient (e.g., determining the family member's condition if the medical condition of the deceased patient is hereditary, etc.).

In one or more embodiments, items that appear under the REPORT, IMAGE, and MEDICINE tabs vary based on whether the SPECIFIC CAUSE or MEDICAL HIST. button is selected. For example, if only the SPECIFIC CAUSE button is selected as shown in FIG. 8A, only items previously categorized as being related to a specific cause of death of the deceased patient is shown under teach of the REPORT, IMAGE, and MEDICINE tabs. On the other hand, if only the MEDICAL HIST. button is selected as shown in FIG. 8B, all items included in the entire medical history of the deceased patient are identified. This would also include the items previously categorized as being related to a specific cause of death of the deceased patient. However, the user will not know which items are directed to a specific cause of death of the deceased patient unless the user has selected only the SPECIFIC CAUSE button. In one or more embodiments, the SPECIFIC CAUSE and MEDICAL HIST. buttons can both be enabled at the same time.

Figure 8C:
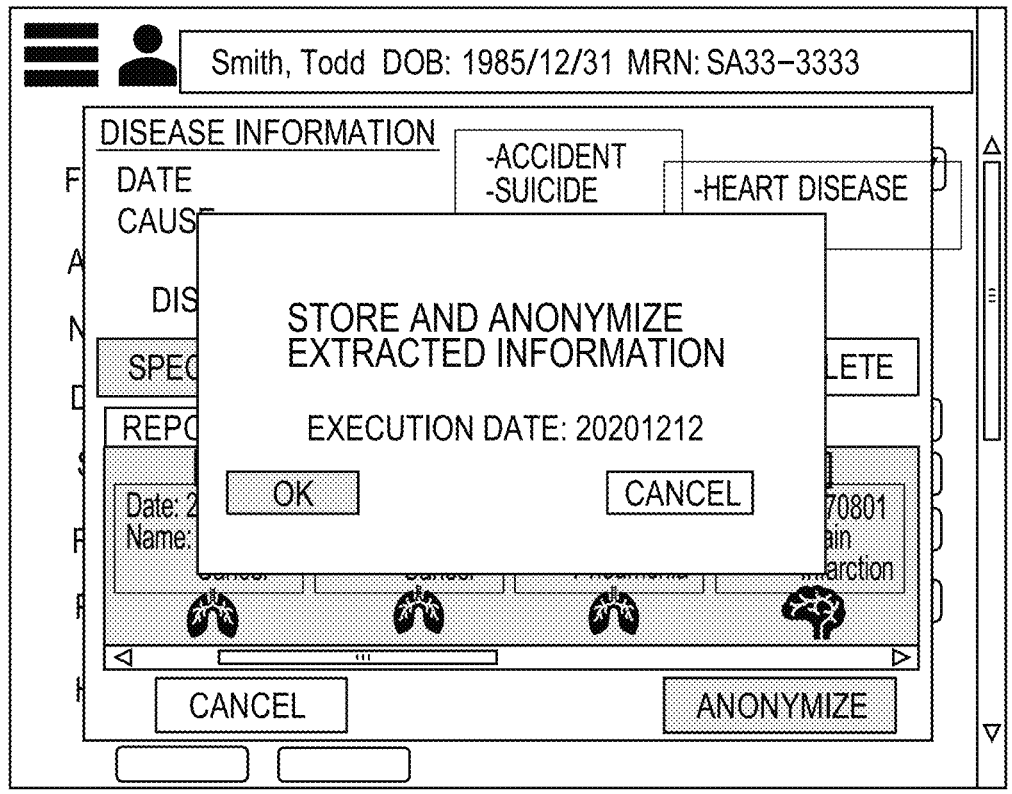
Figure 8D:
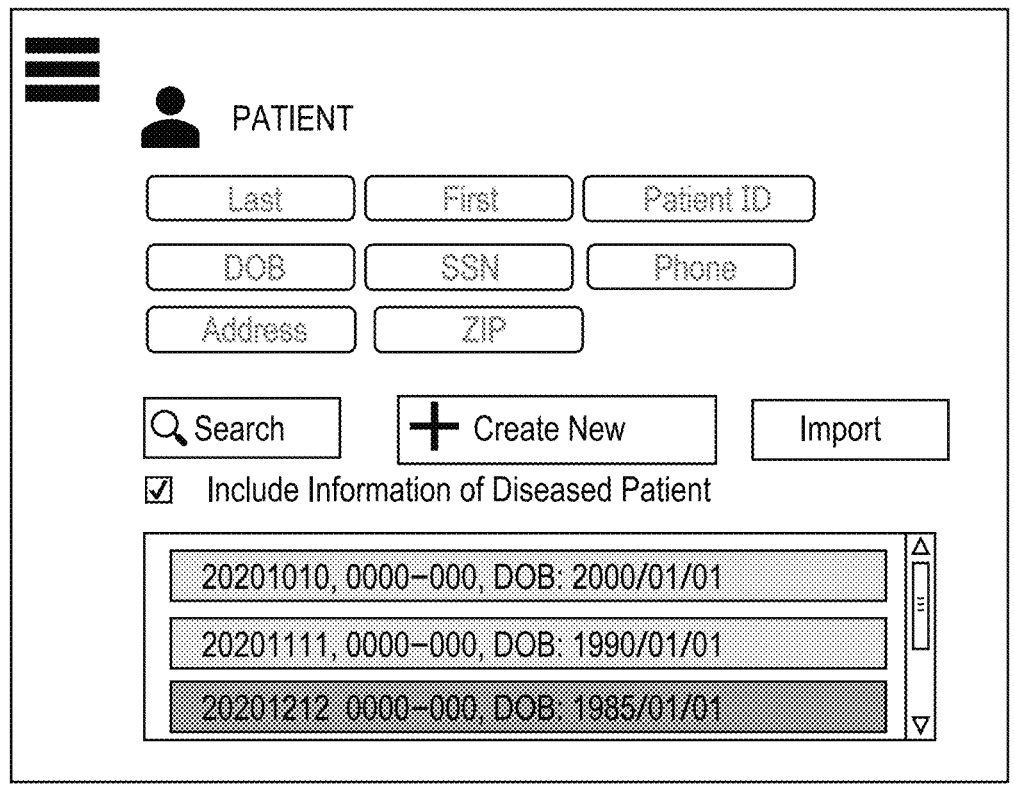

In one or more embodiments, when the extraction is completed, the processor (110) displays a pop-up screen shown in FIG. 8C asking the user whether to store and anonymize the medical condition information. If the user clicks the CANCEL button, the process returns to the extraction screen without storing the extracted medical condition information or deleting the deceased patient medical information. If the user clicks the OK button, the processor (110) separately stores the extracted medical condition information in the storage (120) and deletes the remaining deceased patient medical information from the storage (120).

Figure 8E:

In one or more embodiments, in response to the user clicking on the OK button on the pop-up screen of FIG. 8C, the processor (110) anonymizes the medical condition information. As shown in FIG. 8E, the medical condition information may be anonymized by replacing the patient name with the date of death. The medical condition information may also be anonymized by replacing the date of birth with a preselected date (e.g., 1/1) while retaining the year of birth (e.g., 19XX). By retaining the year of birth, it is possible to conceal the date of birth while still identifying the general age of the deceased patient. Anonymizing the medical condition information protects privacy of the deceased patient while enabling the use of the medical condition information.

In one or more embodiments, the processor (110) may store the medical condition information and delete the remaining deceased patient medical information at different timings. In other words, the remaining deceased patient medical information will not be automatically deleted immediately after the processor (110) finishes extracting and separately storing the medical condition information. In one or more embodiments where the remaining deceased medical information is not automatically deleted immediately after the extraction is completed, the remaining deceased patient medical information may be manually deleted by the user. For example, the user may click on the ALL DELETE button shown in FIGS. 8A-8B to manually delete the remaining deceased patient medical information. In this example, the user may manually click the ANONYMIZE button shown in FIGS. 8A-8C to anonymize the medical condition information. Alternatively, the pop-up screen shown in FIG. 8C will only include an option asking whether the user wishes to anonymize the medical condition information.

After storing and anonymizing the medical condition information, the processor (110) retrieves the anonymized medical condition information upon receiving the medical condition information retrieval request from the local computing device (200A). In one or more embodiments, the search screen shown in FIG. 8D includes a check box indicating "include information of deceased patient." When the user turns on the check box before retrieving the medical condition information, the anonymized medical condition information will also be retrieved and displayed on the search screen. More specifically, anonymized medical condition information will only be retrieved if this check box is enabled (i.e., turned on). When the user clicks on one of the displayed anonymized medical condition information while conducting a medical examination/treatment, the selected anonymized medical condition information is displayed on the edit screen as shown in FIG. 8E.

In one or more embodiments, the screens in FIGS. 7A-7F and 8A-8E can be shown in any language (e.g., Japanese, German, English, etc.). The medical information stored in storage (120) may also be stored in any language. The processor (100) may automatically translate a search keyword entered by the user to find the corresponding medical information in the database.

FIG. 9 shows an example where the anonymized medical condition information is presented in table stored in the database of storage (120). FIG. 9 corresponds to the table shown in FIG. 2 (with the LIFE FLAG and HISTORY FLAG columns removed and a newly added MEDICAL IMAGE column). In FIG. 9, the original medical information of Patient 2 shown in FIG. 2 has been replaced with Patient 2's anonymized medical condition information. Specifically, the original data in the PATIENT NAME column (i.e., "Tim" in FIG. 2) is now shown as Patient 2's date of death. Additionally, the original patient DOB data is now shown as Patient 2's original year of birth with a preselected date of 1/1. The newly added MEDICAL IMAGE column includes a medical image (as the predetermined information or the specified item) extracted from Patient 2's deceased patient medical information.

Also shown in FIG. 9 is an example where a deceased patient's medical information is completely deleted. Referring back to FIG. 2, Patient 3 ("Jenny") is deceased (LIFE FLAG value "2") and previously did not have a serious illness (HISTORY FLAG value "2"). Furthermore, no predetermined information was found during the medical condition information extraction process. Therefore, all of Patient 3's medical information is deleted from the storage (120).

[Method for Control Deletion]

Figure 10:
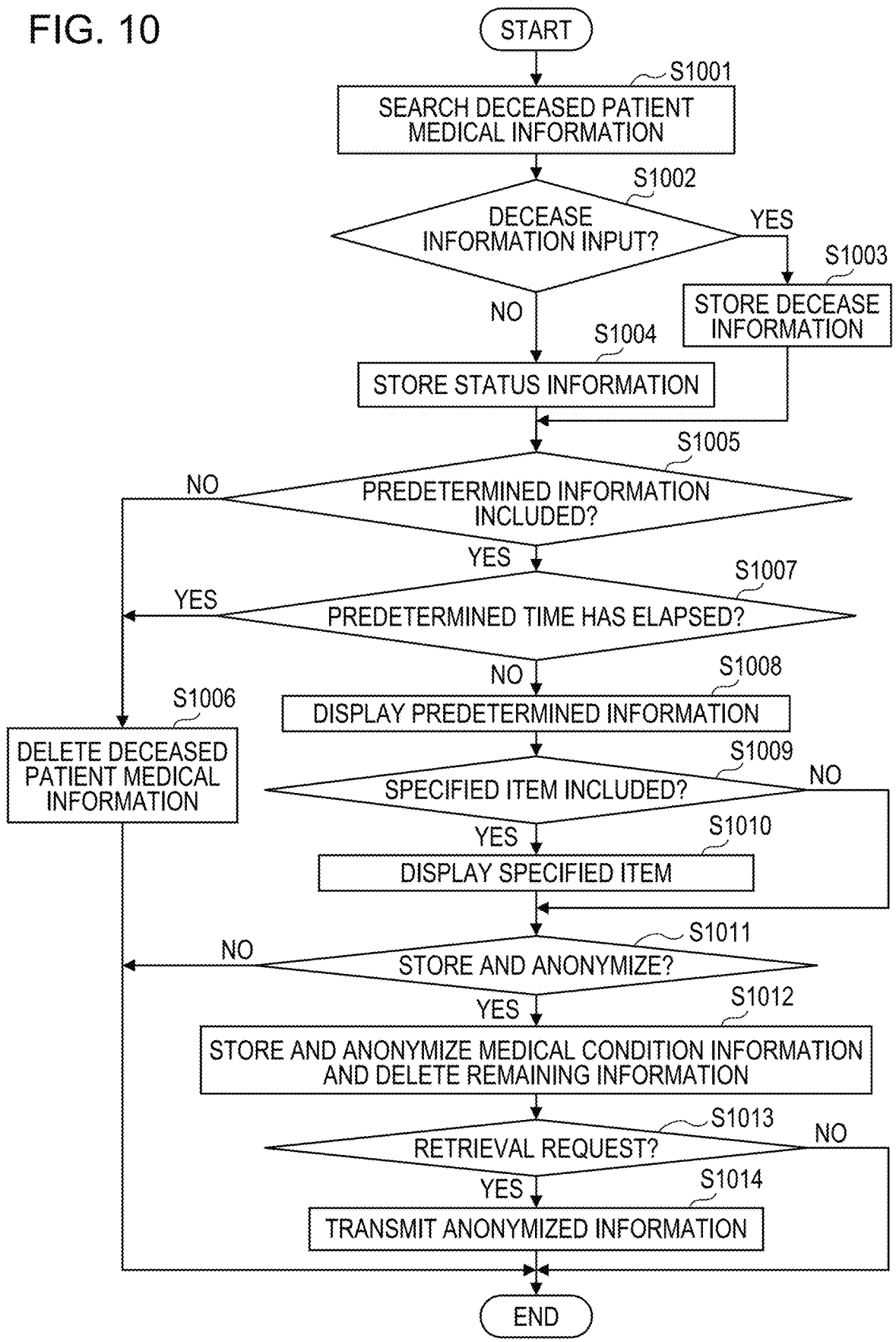
FIG. 10 shows a flowchart according to one or more embodiments.

FIG. 10 shows a flowchart according to one or more embodiments. One or more of the steps in FIG. 10 may be performed by the components of the system 1000, discussed above in reference to FIG. 1. In one or more embodiments, one or more of the steps shown in FIG. 10 may be omitted, repeated, and/or performed in a different order than the order shown in FIG. 10. Accordingly, the scope of the invention should not be considered limited to the specific arrangement of steps shown in FIG. 10.

In Step S1001, a processor (110) receives a patient-identity-specific information of the deceased patient as the search request, and searches (using the patient-identity-specific information as a key) the deceased patient medical information from the storage (120) (Step S1001). In one or more embodiments, the retrieved deceased patient medical information is also displayed on the I/O interface (130).

In Step S1002, the processor (110) determines whether the decease information has been received. As the same time, the processor (110) determines whether the status information has been received. If the decease information has been received (Step S1002: Yes), the processor (110) stores the decease information in the storage (120) (Step S1003). If the decease information has not been received but the status information has been received (Step S1002: No), the processor (100) stores only the status information in the storage (120) (Step S1004).

In Step S1005, the processor (110) determines whether the deceased patient medical information includes the predetermined information. In one or more embodiments, the processor (110) starts the determination in Step S1005 after receiving the start command from the user. For example, the processor (110) may start the determination process after the user clicks the SPECIFIC CAUSE button in FIG. 8A or the MEDICAL HISTORY in FIG. 8B. Alternatively, the processor may automatically start the determination process upon receiving information that the patient is deceased (e.g., upon receiving the decease information entered on the input screen of FIG. 7F).

If the deceased patient medical information does not include the predetermined information (Step S1005: No), the processor (110) deletes the deceased patient medical information from the storage (120) (Step S1006).

If the deceased patient medical information includes the predetermined information (Step S1005: Yes), the processor (110) starts a timer and determines whether a predetermined time has elapsed since the start of the timer (Step S1007). If the predetermined time has elapsed (Step S1007: Yes), the processor (110) deletes the deceased patient medical information (Step S1006) regardless of whether the predetermined information has been extracted.

If the predetermined time has not elapsed (Step S1007: No), the processor (110) extracts the predetermined information along with the patient-identity-specific information of the deceased patient from the deceased patient medical information and displays the extracted predetermined information and patient-identity-specific information as the medical condition information on the I/O interface (130) (Step S1008).

In Step S1009, upon receiving the user input of the specified item, the processor (110) determines whether the predetermined information includes the specified item. If the predetermined information does not include the specified item (Step S1009: No), the processing proceeds to Step S1011. If the predetermined information includes the specified item (Step S1009: Yes), the processor (110) extracts the specified item from the predetermined information and displays the extracted specified item as the medical condition information instead of the predetermined information (Step S1010).

In STEP S1011, the processor (110) determines whether to store and anonymize the medical condition information based on a user input via the I/O interface (130). When determining not to store and anonymize the medical condition information (Step S1011: No), the processor (110) terminates the processing.

When determining to store and anonymize the medical condition information (Step S1011: Yes), the processor (110) (in Step S1012) stores and anonymizes the medical condition information and deletes the remaining deceased patient medical information from the storage (120).

In Step S1013, after storing and anonymizing the medical condition information, the processor (110) determines whether the medical condition information retrieval request has been received from the local computing device (200A) (Step S1013). Upon determining that the medical condition information retrieval request has not been received (Step S1013: No), the processor (110) terminates the processing. Upon determining that the medical condition information retrieval request has been received (Step S1013: Yes), the processor (110) transmits in Step S1014 the anonymized medical condition information to the local computing device (200A). In one or more embodiments, the processor (210A) of the local computing device (200A) displays the received anonymized medical condition information on the I/O interface (230A) of the local computing device (200A).

Figure 11:
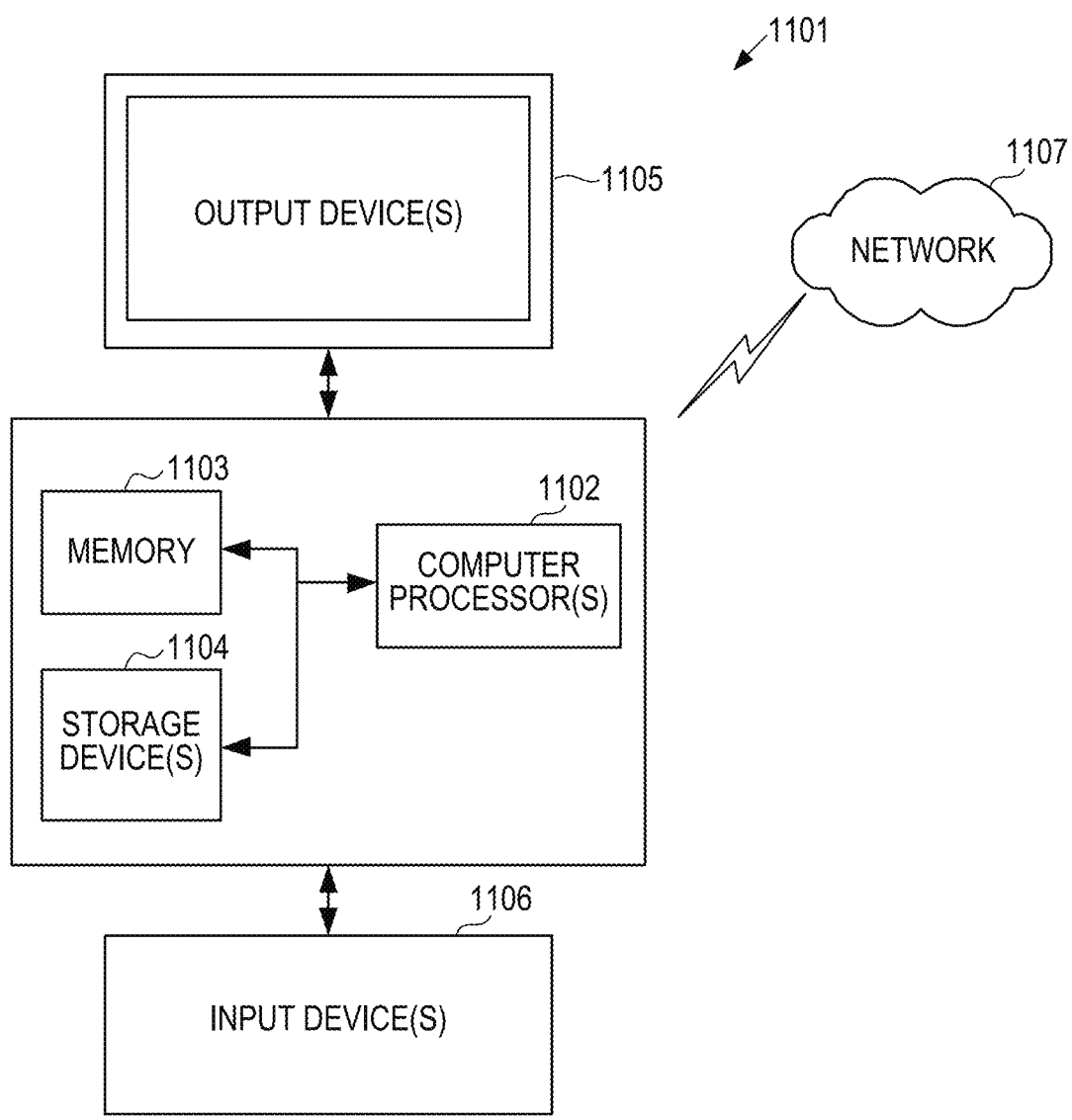
FIG. 11 shows a computing system in accordance with one or more embodiments.

Embodiments of the invention may be implemented on virtually any type of computing system, regardless of the platform being used. For example, the computing system may be one or more mobile devices (e.g., laptop computer, smart phone, personal digital assistant, tablet computer, or other mobile device), desktop computers, servers, blades in a server chassis, or any other type of computing device or devices that includes at least the minimum processing power, memory, and input and output device(s) to perform one or more embodiments. For example, as shown in FIG. 11, the computing system (1101) may include one or more computer processor(s) (1102), associated memory (1103) (e.g., random access memory (RAM), cache memory, flash memory, etc.), one or more storage device(s) (1104) (e.g., a hard disk, an optical drive such as a compact disk (CD) drive or digital versatile disk (DVD) drive, a flash memory stick, etc.), and numerous other elements and functionalities. The computer processor(s) (1102) may be an integrated circuit for processing instructions. For example, the computer processor(s) may be one or more cores, or micro-cores of a processor. The computing system (1101) may also include one or more input device(s) (1106), such as a touchscreen, keyboard, mouse, microphone, touchpad, electronic pen, or any other type of input device. Further, the computing system (1101) may include one or more output device(s) (1105), such as a screen (e.g., a liquid crystal display (LCD), a plasma display, touchscreen, cathode ray tube (CRT) monitor, projector, or other display device), a printer, external storage, or any other output device. One or more of the output device(s) may be the same or different from the input device(s). The computing system (1101) may be connected to a network (1107) (e.g., a local area network (LAN), a wide area network (WAN) such as the Internet, mobile network, or any other type of network) via a network interface connection (not shown). The input and output device(s) may be locally or remotely (e.g., via the network (1107)) connected to the computer processor(s) (1102), memory (1103), and storage device(s) (1104). Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform embodiments of the invention.

Further, one or more elements of the aforementioned computing system (1101) may be located at a remote location and connected to the other elements over a network (1107). Further, one or more embodiments of the invention may be implemented on a distributed system having a plurality of nodes, where each portion of the invention may be located on a different node within the distributed system. In one embodiment of the invention, the node corresponds to a distinct computing device. Alternatively, the node may correspond to a computer processor with associated physical memory. The node may alternatively correspond to a computer processor or micro-core of a computer processor with shared memory and/or resources.

The management server, method, and non-transitory computer readable medium of one or more embodiments provide various improvements to information management technologies in the medical field.

For example, the memory space in the cloud server and/or local servers storing the medical information is advantageously conversed by deleting the deceased patient medical information from which information useful to physicians after the patient's death (e.g., information related to the cause of death and/or medical history information) has been extracted.

Retaining only information related to the cause of death and/or medical history information also advantageously improves a review time of the deceased patient medical information by the deceased patient's primary treating physician and/or another physician reviewing the deceased patient's records.

Further, retention of such information after the patient's death while deleting other remaining information advantageously improves a diagnosis time and diagnosis effect on a family member of the deceased patient. For example, a physician treating a deceased patient's family member is able to timely and accurately identify a sickness/disease (e.g., high blood pressure, diabetes, HIV etc.) experienced by the family member by consulting the cause of death and medical history of the deceased patient. Even further, anonymizing the extracted information protects privacy of the deceased patient while enabling the use of the extracted information.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A management server that communicates with a healthcare facility, the management server comprising:
    a storage that stores medical information including patient-identity-specific information; and
    a processor coupled to the storage, wherein the processor:
        receives patient-identity-specific information of a deceased patient;
        retrieves, from among the medical information in the storage, a deceased patient medical information using the patient-identity-specific information of the deceased patient;
        determines whether the deceased patient medical information includes a predetermined information that specifies a medical condition of the deceased patient;
        upon determining that the deceased patient medical information does not include the predetermined information, deletes the deceased patient medical information from the storage;
        upon determining that the deceased patient medical information includes the predetermined information:
            extracts the predetermined information along with the patient-identity-specific information of the deceased patient from the deceased patient medical information;
            separately stores the extracted predetermined information and the patient-identity-specific information of the deceased patient in the storage as a medical condition information; and
            deletes the deceased patient medical information after the extraction and storage of the medical condition information; and
        transmits, upon receiving a medical condition information retrieval request from the healthcare facility, the medical condition information to the healthcare facility to be displayed on a display of the healthcare facility.

2. The management server according to claim 1, wherein the processor further:
    determines whether a decease information has been received, wherein the decease information includes a cause of death of the deceased patient;
    upon determining that the decease information has been received, stores the decease information in the storage; and
    upon determining that the decease information has not been received but a status information has been received, stores the status information in the storage, wherein the status information indicates whether each patient recorded in the management server is deceased or alive.

3. The management server according to claim 1, wherein the processor further:
    in response to determining that the deceased patient medical information includes the predetermined information, determines whether a predetermined time has elapsed; and
    upon determining that the predetermined time has elapsed, deletes the deceased patient medical information regardless of whether the predetermined information has been extracted.

4. The management server according to claim 1, wherein the processor further:
    upon determining that the deceased patient medical information includes the predetermined information, determines whether the predetermined information includes a specified item; and
    upon determining that the predetermined information includes the specified item, extracts the specified item from the predetermined information and stores the specified item as the medical condition information instead of the predetermined information.

5. The management server according to claim 1, wherein the patient-identity-specific information includes a patient name and a date of birth, and
the processor anonymizes the patient-identity-specific information by one or both of:
    replacing the patient name with a date of death, and
    replacing the date of birth with a preselected date.

6. A method for controlling deletion of medical information from a storage of a management server that communicates with a healthcare facility, the storage storing medical information including patient-identity-specific information, the method comprising:
    receives a patient-identity-specific information of a deceased patient;
    retrieves, from among the medical information in the storage, a deceased patient medical information using the patient-identity-specific information of the deceased patient;
    determining whether the deceased patient medical information includes a predetermined information that specifies a medical condition of the deceased patient;
    upon determining that the deceased patient medical information does not include the predetermined information, deleting the deceased patient medical information from the storage;
    upon determining that the deceased patient medical information includes the predetermined information:

extracting the predetermined information along with the patient-identity-specific information of the deceased patient from the deceased patient medical information,
separately storing the extracted predetermined information and the patient-identity-specific information of the deceased patient in the storage as a medical condition information, and
deleting the deceased patient medical information after the extraction and storage of the medical condition information; and
transmitting, upon receiving a medical condition information retrieval request from the healthcare facility, the medical condition information to the healthcare facility to be displayed on a display of the healthcare facility.

7. The method according to claim 6, further including:
determining whether a decease information has been received, wherein the decease information includes a cause of death of the deceased patient,
upon determining that the decease information has been received, storing the decease information in the storage, and
upon determining that the decease information has not been received but a status information has been received, storing the status information in the storage, wherein the status information indicates whether each patient recorded in the management server is deceased or alive.

8. The method according to claim 6, further comprising:
in response to determining that the deceased patient medical information includes the predetermined information, further determining whether a predetermined time has elapsed; and
upon determining that the predetermined time has elapsed, deleting the deceased patient medical information regardless of whether the predetermined information has been extracted.

9. The method according to claim 6, further comprising:
upon determining that the deceased patient medical information includes the predetermined information, determining whether the predetermined information includes a specified item, and
upon determining that the predetermined information includes the specified item, extracting the specified item from the predetermined information and storing the specified item as the medical condition information instead of the predetermined information.

10. The method according to claim 6, wherein
the patient-identity-specific information includes a patient name and a date of birth, and
the method further comprises:
anonymizing the patient-identity-specific information by one or both of:
replacing the patient name with a date of death, and
replacing the date of birth with a preselected date.

11. A non-transitory computer-readable medium (CRM) storing an instruction to control deletion of medical information from a storage of a management server that communicates with a healthcare facility, the storage storing medical information including patient-identity-specific information, the instruction causing a management server to:
receive a patient-identity-specific information of a deceased patient;
retrieve, from among the medical information in the storage, a deceased patient medical information using the patient-identity-specific information of the deceased patient;
determine whether the deceased patient medical information includes a predetermined information that specifies a medical condition of the deceased patient;
upon determining that the deceased patient medical information does not include the predetermined information, delete the deceased patient medical information from the storage;
upon determining that the deceased patient medical information includes the predetermined information:
extract the predetermined information along with the patient-identity-specific information of the deceased patient from the deceased patient medical information,
separately store the extracted predetermined information and the patient-identity-specific information of the deceased patient in the storage as a medical condition information, and
delete the deceased patient medical information after the extraction and storage of the medical condition information; and
transmit, upon receiving a medical condition information retrieval request from the healthcare facility, the medical condition information to the healthcare facility to be displayed on a display of the healthcare facility.

12. The non-transitory CRM according to claim 11, wherein
the instruction further causes a management server to:
determine whether a decease information has been received, wherein the decease information includes a cause of death of the deceased patient;
upon determining that the decease information has been received, store the decease information in the storage; and
upon determining that the decease information has not been received but a status information has been received, store the status information in the storage, wherein the status information indicates whether each patient recorded in the management server is deceased or alive.

13. The non-transitory CRM according to claim 11, wherein
the instruction further causes a management server to:
in response to determining that the deceased patient medical information includes the predetermined information, determine whether a predetermined time has elapsed; and
upon determining that the predetermined time has elapsed, delete the deceased patient medical information regardless of whether the predetermined information has been extracted.

14. The non-transitory CRM according to claim 11, wherein
the instruction further causes a management server to:
upon determining that the deceased patient medical information includes the predetermined information, determine whether the predetermined information includes a specified item; and
upon determining that the predetermined information includes the specified item, extract the specified item from the predetermined information and store the specified item as the medical condition information instead of the predetermined information.

15. The non-transitory CRM according to claim 11, wherein
the patient-identity-specific information includes a patient name and a date of birth, and the instruction further causes a management server to anonymize the patient-identity-specific information by one or both of:
replacing the patient name with a date of death, and
replacing the date of birth with a preselected date.

* * * * *